(12) United States Patent
Auvenshine et al.

(10) Patent No.: US 9,773,401 B1
(45) Date of Patent: Sep. 26, 2017

(54) CLOSE RANGE MONITORING

(71) Applicant: International Business Machines Corporation, Armonk, NY (US)

(72) Inventors: John J. Auvenshine, Tucson, AZ (US); Perry J. Gallo, Tucson, AZ (US); Scott W. Hughes, Foundtain Inn, SC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/175,129

(22) Filed: Jun. 7, 2016

(51) Int. Cl.
*G08B 1/00* (2006.01)
*G08B 21/18* (2006.01)
*H04B 1/3827* (2015.01)
*H04W 76/02* (2009.01)
*H04W 4/00* (2009.01)
*G08B 3/10* (2006.01)
*G08B 5/22* (2006.01)
*G08B 21/02* (2006.01)
*A61B 5/024* (2006.01)
*A61B 5/00* (2006.01)

(52) U.S. Cl.
CPC ........ *G08B 21/182* (2013.01); *A61B 5/02438* (2013.01); *A61B 5/681* (2013.01); *G08B 3/10* (2013.01); *G08B 5/22* (2013.01); *G08B 21/0211* (2013.01); *H04B 1/385* (2013.01); *H04W 4/005* (2013.01); *H04W 4/008* (2013.01); *H04W 76/02* (2013.01)

(58) Field of Classification Search
CPC .............. G08B 21/182; G08B 21/0225; G08B 21/0269

USPC ......... 340/532, 539.12, 539.21, 573.4, 686.6
See application file for complete search history.

(56) References Cited

U.S. PATENT DOCUMENTS

| | | | |
|---|---|---|---|
| 6,104,293 | A | 8/2000 | Rossi |
| 7,009,512 | B2 | 3/2006 | Cordoba |
| 7,348,880 | B2 | 3/2008 | Hules et al. |
| 8,212,672 | B2 | 7/2012 | Brenner |
| 8,232,874 | B1 | 7/2012 | Aneiros et al. |
| 8,878,673 | B2 | 11/2014 | Grant et al. |
| 2005/0280546 | A1* | 12/2005 | Ganley .............. G08B 13/1427 340/573.4 |
| 2011/0092161 | A1* | 4/2011 | Dotan ................ G08B 21/0225 455/41.3 |
| 2013/0049955 | A1 | 2/2013 | Hoover et al. |
| 2015/0109126 | A1* | 4/2015 | Crawford ........... G08B 21/0269 340/539.13 |

(Continued)

OTHER PUBLICATIONS

Unknown, "Temperature Measurements with Thermistors: How-To Guide", National Instruments, Published Apr. 2015, © 2016 National Instruments, 3 pages.

(Continued)

*Primary Examiner* — Tai T Nguyen
(74) *Attorney, Agent, or Firm* — Laura E. Gisler (57) ABSTRACT

A wearable device may connect to a wearable device over a short-range wireless connection. The user device may receive sensor data from the wearable device, where the wearable device has sensors. The user device may determine that a safety alert parameter has been met, and in response generate an audible alarm. The device may then determine that the connection between the user device and the wearable device has been disconnected, and in response, generate a second audible alarm.

10 Claims, 6 Drawing Sheets

(56) References Cited

U.S. PATENT DOCUMENTS

2015/0274036 A1    10/2015    Arad et al.

OTHER PUBLICATIONS

Unknown, "Driver's Little Helper: Simple Car Seat Safety", Driver's Little Helper, 6 pages, Last printed Feb. 18, 2016. https://driverslittlehelper.com/.
Unknown, "Bluetooth Tracking Devices, Location Tracking Technology", Tracking Sticker, © Tracking Sticker 2016, 2 pages. Last printed Feb. 18, 2016. http://www.trackingsticker.com.
Unknown, "Swimming Pool Alarm", Brickhouse Security, 2 pages. Last printed Feb. 18, 2016. http://www.brickhousesecurity.com/product/swimming+pool+alarm.do.
Unknown, "FAQ", My BuddyTag, © 2016 Le Vise Products LLC, 5 pages. Last printed on Feb. 18, 2016. http://www.mybuddytag.com/faq/.
Unknown, "Evenflo", © 2015 Evenflo Company, Inc., 4 pages.
Unknown, "My BuddyTag", © 2016 Le Vise Products LLC, 3 pages, Last printed on Feb. 29, 2016. http://www.mybuddytag.com/.
Unknown, "Smart Technology for Your Child's Car Seat", Car Seat Monitor, Cars-N-Kids, Last printed Jun. 6, 2016, 5 pages. https://carseatmonitor.com/.

* cited by examiner

CLOSE RANGE MONITORING

BACKGROUND

The present disclosure relates to close range monitoring, and more specifically, to close range data exchange for safety monitoring.

Wireless technology may exist to exchange data over short distances. In some cases, this data may be exchanged from fixed or mobile devices using short-wavelength radio waves. Based on settings, these wireless signals may range anywhere from under one meter to over 100 meters. Many mobile devices such as smart phones may have a range of approximately 10 meters in any direction.

Wearable technology, or "wearables" may be clothing or accessories which incorporate computer and advanced electronic technologies. The wearables are often designed to incorporate practical functions and feature. For example, "activity trackers" can be used to monitor the activity level of a particular user, based on, for example, steps taken or a monitored heart rate. Wearables may also be used to improve child safety, where the technology may be worn by a child to monitor his or her activity or location, in order to avoid a dangerous situation.

SUMMARY

Embodiments of the present disclosure may be directed toward a method which may begin by connecting a user device to a wearable device over a short-range wireless connection. In embodiments, the user device may receive sensor data from the wearable device and through the short-range wireless connection. The sensor data may be collected by at least one sensor on the wearable device. The user device may determine that a safety alert parameter has been met based on the received sensor data, and in response, generate a first audible alarm. The device may then determine that the connection between the user device and the wearable device has been connected, and in response, generate a second audible alarm.

Embodiments of the present disclosure may be directed toward a method that begins when a user device is detected by a wearable device. The user device may be detected as within range of a short-range wireless connection of the wearable device. The wearable device may have a set of sensors. The wearable may then connect with the user device over the network. Environment data may then be connected from the set of sensors around the wearable, and receive safety alert parameter data from the user device. The safety alert parameter data may have a set of parameters that can be used to determine that a condition is unsafe. In response to determining that a safety alert parameter has been met, the wearable may generate a first audible alarm. The system may then generate a second audible alarm, in response to a determination that the user device has disconnected from the wearable.

Embodiments of the present disclosure may be directed toward a computer system comprising a computer readable storage medium with program instructions stored thereon, a speaker, and one or more processors configured to execute the program instructions to perform a method. The method may begin by connecting a user device to a wearable device over a short-range wireless connection. In embodiments, the user device may receive sensor data from the wearable device and through the short-range wireless connection. The sensor data may be collected by at least one sensor on the wearable device. The user device may determine that a safety alert parameter has been met based on the received sensor data, and in response, generate a first audible alarm. The device may then determine that the connection between the user device and the wearable device has been connected, and in response, generate a second audible alarm.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to close range monitoring, more particular aspects relate to close range data exchange for safety monitoring. While the present disclosure is not necessarily limited to such applications, various aspects of the disclosure may be appreciated through a discussion of various examples using this context.

In embodiments, a user device such as a smart phone may possess short-range wireless network capabilities through the use of, for example, a BLUETOOTH application. The device may then be paired with second short-range wireless network (e.g., BLUETOOTH) enabled device. This second device could be a wearable device or a clip, for example a pedometer, heart rate monitor, smart watch, or a simple BLUETOOTH-enabled clip. For ease of discussion, this second device will be referred to as a "wearable" herein. For example, the wearable may be attached to a child's clothing or wrist. The user device and the wearable may exchange data while paired over the network. At some point, the wearable or the smart phone may be out of range (e.g., of the short-range wireless connection or BLUETOOTH network). This may result in the disconnection of the user device with the wearable, and thus the cessation of data transfer between the wearable and the user device. This disconnection can be recognized by a system (for example, a computer system that may be embodied within the user device), and in response to the recognition, an audible alert can be by the user device. In embodiments, safety parameters, including temperature for a duration of time (e.g., a combination of a temperature parameter and a timing parameter), the presence of moisture, or other parameters which may indicate an unsafe condition based on the context of the user of the user device and the wearable, and may generate an alarm on the user device.

In embodiments, the wearable may have one or more sensors, in addition to possessing short-range wireless network capabilities. For example, the wearable could have a temperature sensor to detect the temperature of the environment surrounding the wearable or to detect the temperature of the individual in possession of the wearable. The wearable could also have a moisture sensor or sensors, which could be used to detect the presence of water at the location of the wearable. Various configurable parameters could be set to define, based on the user, environment, and intent of use, a set of unsafe conditions, as determined based on sensor data. For example, a detection of a temperature below 65° F. or above 75° F. could meet a safety parameter, which could indicate to the user that the wearable is in an unsafe condition. The safety parameter could also factor time into its determination, for example, by requiring that the sensor detect a particular temperature for a certain period of time in order to meet a safety alert parameter.

Figure 1:
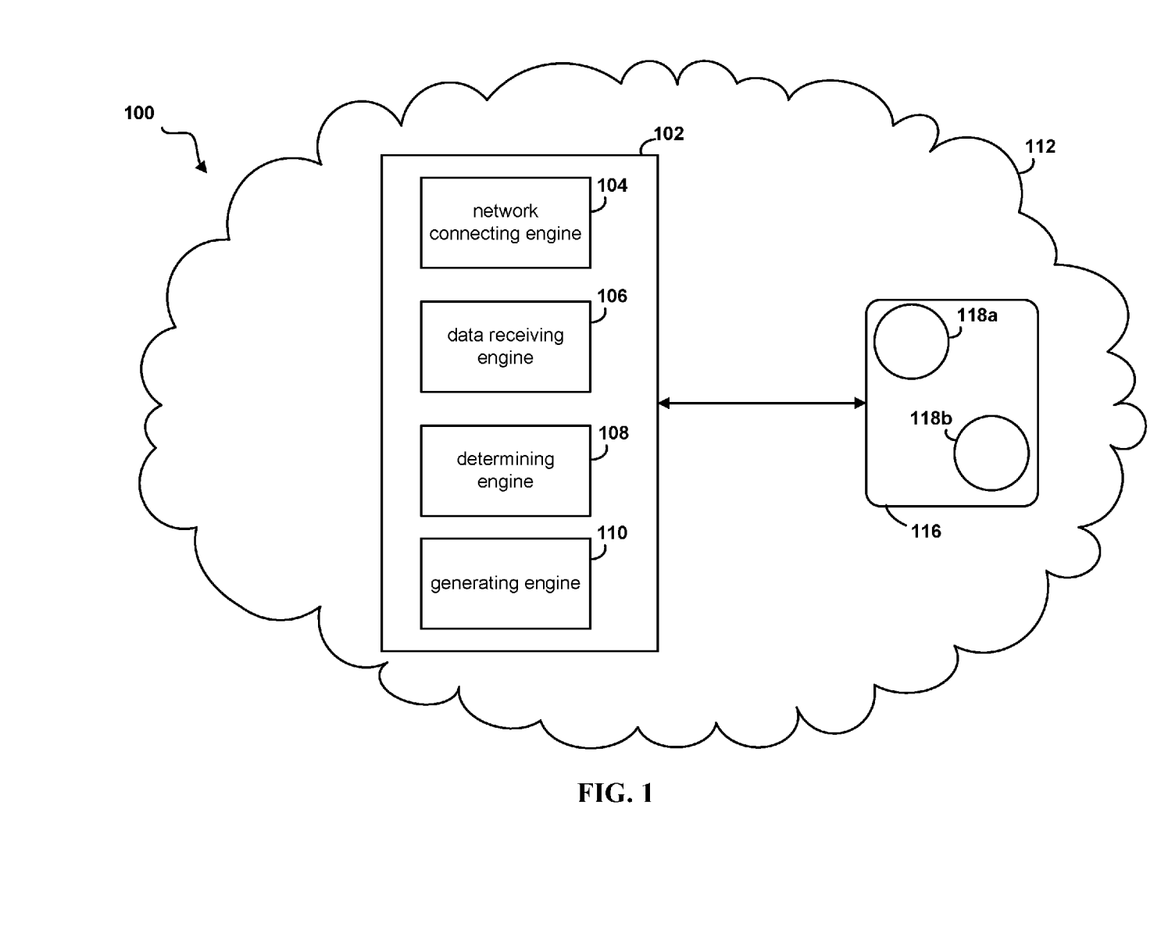
FIG. 1 depicts a system diagram of a system for alerting a user to an unsafe condition over a short-range wireless connection, according to embodiments.

FIG. 1 depicts a system diagram of a system 100 for alerting a user to an unsafe condition over a short-range wireless network connection 112, according to embodiments. A computer system 102 may comprise a number of engines 104-110. The actions performed by the engines may be executed by one or more processors, for example, the processors of computer system 600 of FIG. 6. In embodiments, the computer system 102 may be embodied in a user device such as a smart phone, tablet, laptop computer, or device. The computer system 102 may be connected to a wearable device or "wearable" 116 via a wireless network connection 112. The network connection 112 may be a short-range wireless connection, for example, a BLUETOOTH network.

In embodiments, the network connecting engine 104 may detect a wearable 116 is within range of the network connection 112. The network connecting engine 104 may then connect with the wearable 116 by "pairing" with it over the short-range wireless connection 112. The wearable 116 may have one or more sensors 118a and 118b. In embodiments, these sensors 118 may be temperature sensors, moisture sensors, or other sensors. The sensors 118 may be installed on, as a part of, the wearable or they may communicatively coupled to the wearable.

Upon establishing a connection with the wearable 116, the wearable 116 may begin to send sensor data to the computer system 102. In embodiments, this can be a consistent transmission of sensor data from the wearable 116 to the computer system 102. This data can be received by the data receiving engine 106 of the computer system 102. In embodiments, the computer system 102 can also send data to the wearable 116. This data can be sent by the data receiving engine 106, or by another engine.

Based on the data received from the sensors 118 or the wearable 116, the computer system 102 may determine that a safety alert parameter has been met. In embodiments, the safety alert parameter may be one of a set of parameters ranging from temperature extremes determined unsafe and configured by a user or system administrator to the presence of moisture for a predetermined period of time. In embodiments, the absence of data transmission between the wearable 116 and the computer system 102 may meet a safety alert parameter, as the cessation of data transmission may indicate that the wearable 116 and the computer system 102 are no longer connected over the short-range wireless connection 112. In embodiments, the network connecting engine 104 of the computer system 102 could detect that the computer system 102 is no longer connected to the wearable 116 over the wireless network 112.

In embodiments, this could indicate that the wearable 116, and thus the user of the wearable, has moved outside of the short-range wireless connection 112 or BLUETOOTH range of connectivity. In embodiments, this disconnection could indicate an unsafe condition for the user of the wearable. For example, the wearable 116 may be worn by a child at a playground, and the computer system 102 could be embodied in a smartphone owned by a parent of the child. The child may be safe playing near the parent, but upon reaching a distance outside the close range BLUETOOTH network, or approximately 30 feet, the wearable will disconnect from the smart phone, indicating that the child is beginning to wander too far from the parent in possession of the previously paired smart phone.

In embodiments, once the determining engine 108 has determined that a particular safety alert parameter has been met, for example, an unsafe temperature as detected from the sensor data, the generating engine 110 of the computer system 102 may generate an audible alarm. In embodiments, the computer system 102 embodied in a smart phone may generate a tone or other alarm. In embodiments, the disconnection of the computer system 102 from the wearable 116 may also cause the wearable to alert the user via the generation of an alarm.

Figure 2:
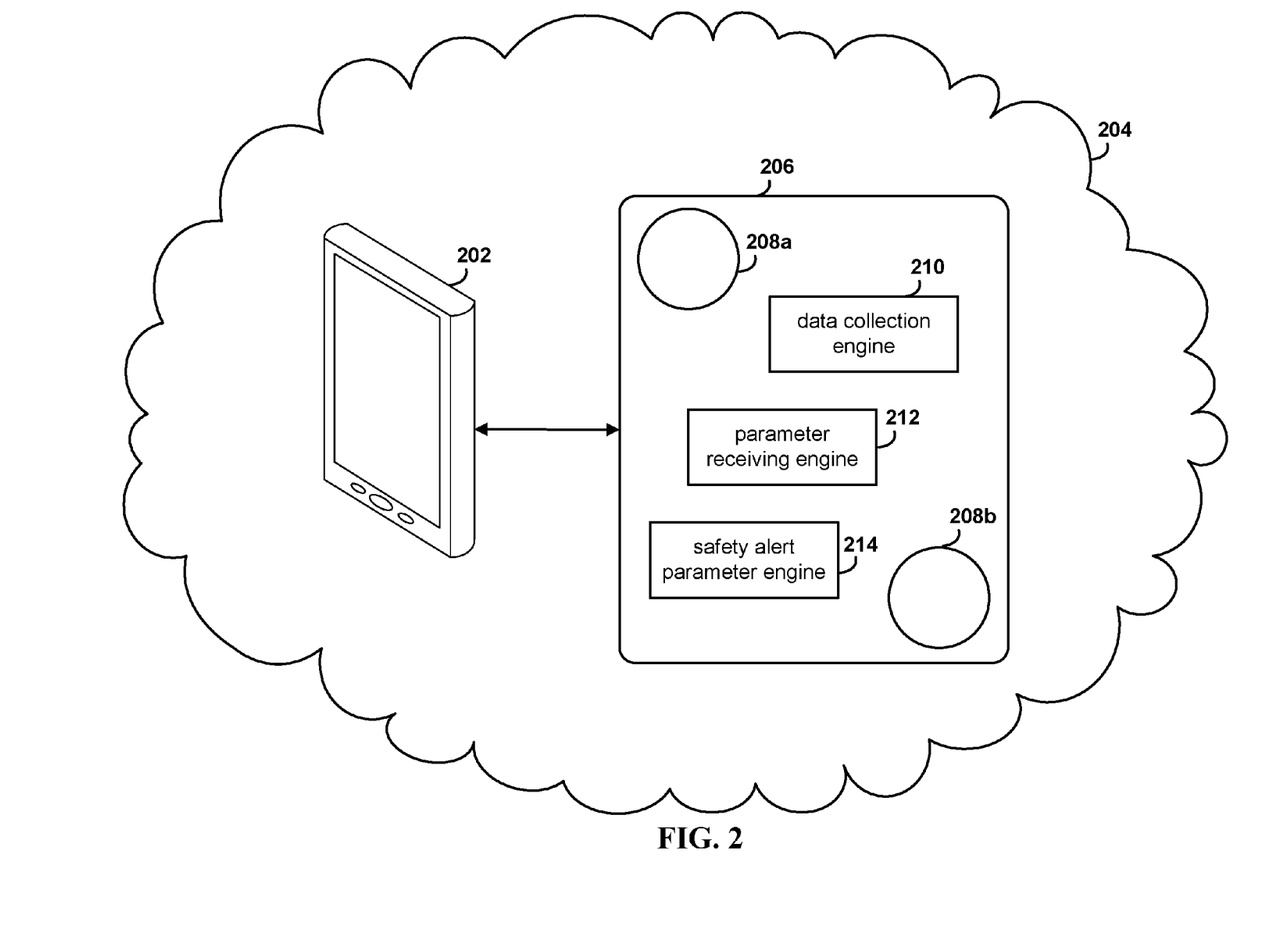
FIG. 2 depicts a system diagram of a system for alerting a user of a wearable to an unsafe condition, according to embodiments.

FIG. 2 depicts a system diagram of a system 200 for alerting a user of a wearable to an unsafe condition, according to embodiments. Like elements may correspond to like elements with those in FIG. 1.

A user device 202 could be, for example, a smartphone. This smartphone could embody a computer system, for example, computer system 102 of FIG. 1. The user device 202 could be connected to a wearable 206, over a network 204, such as a BLUETOOTH or short-range wireless connection. In embodiments, the wearable could be the wearable 116 of FIG. 1. The wearable 206 could have a set of sensors 208. These sensors could be configured to detect various environmental changes. For example, sensor 208a could detect environmental temperature, and sensor 208b could detect the presence of moisture. In embodiments, the wearable 206 could also comprise a variety of engines, which could execute on, for example, a computer processing circuit, instructions regarding detecting for unsafe conditions and alerting a user accordingly.

In embodiments, the wearable 206 could detect a user device 202 within a short-range wireless connection 204. The wearable could connect with the user device 202. In embodiments, this connecting of the wearable 206 and the user device 202 may occur automatically (i.e., without further user intervention) upon the user device 202 entering the short-range wireless connection (or BLUETOOTH network) range for the wearable. In other embodiments, the wearable 206 may prompt a user to connect to the user device 202. For example, if the user device 202 is recognized by the wearable 206, as one that has paired in the past, the wearable 206 could connect automatically, while an unrecognized user device 202 may prompt a user and require further confirmation, a password, or other confirmation of connection.

In embodiments, and upon establishing connection with the user device 202, a parameter receiving engine 212 of the wearable 206 may begin collecting, from the set of sensors on the wearable, environment data. This environment data can vary, depending on the type of wearable 206 as well as the types of sensors 208 installed on the wearable 206. Also upon establishing connection, a parameter receiving engine 212 of the wearable 206 may begin to receive, from the user device 202, safety alert parameter data. In embodiments, this safety parameter alert data may be a set of parameters for determining that a condition is unsafe. For example, these parameters may include particular temperatures that are unsafe for a child or a pet. The parameters may also include a particular period of time at which the temperatures must be sustained at the sensor or sensors. In embodiments, a safety alert parameter engine 214 may processes these parameters and compare them with the environment data captured by the sensors. In embodiments, the environment data and the safety parameter alert data may be stored on the wearable 206. In embodiments, the environment data may be transmitted to the user device 202, for storage. In embodiments, the safety parameter alert data may be set based on user input to the user device, stored on the user device 202, and transmitted to the wearable 206.

The safety alert parameter engine 214 can then determine, based on a comparison between the processed environment data and the safety parameter alert data, that a safety alert parameter has been met. In embodiments, an alarm may be generated by the wearable in response to this determination. For example, sensors 208a and 208b could each detect that it is in the presence of moisture. The safety alert parameter engine 214 can compare this environment data (presence of moisture) with a safety parameter received from the user device 202, and determine that a safety alert parameter has been met. In embodiments, an alarm can then be generated by the wearable. In some cases, this generation could include the transmission of a signal to a speaker on the wearable to cause the wearable to play a tone or an alarm. In other instances, this could generate a signal that may be transmitted across the network 204, if still connected, to cause the user device 202 to sound an audible alarm (via, for example, speakers on a smartphone). In embodiments, the safety alert parameter engine 214 may detect that it is no longer connected to the user device 202 over the short-range wireless connection 204. This may cause the wearable 206 to generate an audible alarm, indicating, for example, the wearable 206 is no longer within a safe distance of the user device 202. For example, in a public park, the range of the short-range wireless connection could be considered a safe distance between a child and his parent.

Figure 3:
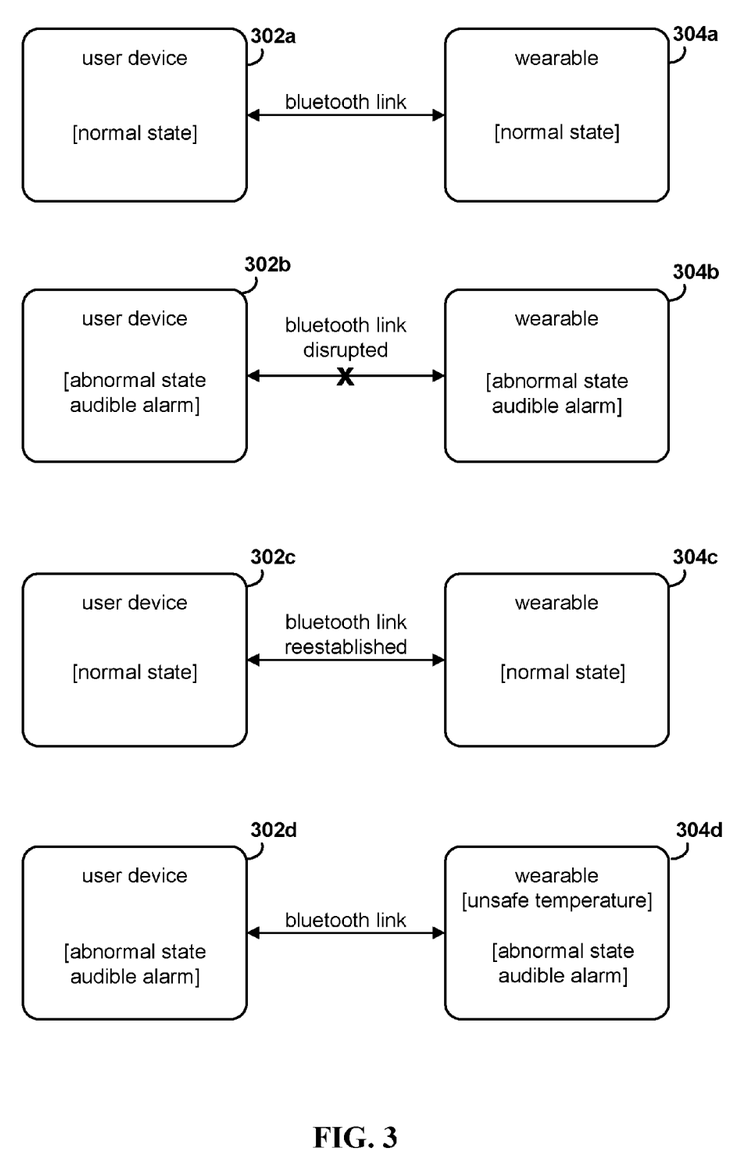
FIG. 3 depicts a block diagram of a use case for generating an alert based on network connectivity, according to embodiments.

FIG. 3 depicts a block diagram of a use case for generating an alert based on network connectivity, according to embodiments. The figure depicts a user device 302 in various states of connectivity with a wearable 304, and the resulting states of each of the user device 302 and wearable 304, based on connectivity and/or sensor data. In embodiments, the user device 302 may be the same as the user device 202 of FIG. 2, or a device on which the computer system 102 of FIG. 1 may be embodied. In embodiments, the wearable 304 may be the wearable 206 of FIG. 2 or the wearable 116 of FIG. 1.

The user device 302a connected, via a BLUETOOTH link, to a wearable 304a. In this case, the connected user device 302a is in a "normal" state (i.e., non-alarm state), as is the wearable 304a. The two devices may have paired over the BLUETOOTH network and may now be able to transmit data, receive data, or both.

The user device 302b is disconnected from the wearable 304b. In this case, the disconnection may have occurred via a disrupted BLUETOOTH link, which could be resultant from one of the wearable 304b or the user device 302b moving outside of the BLUETOOTH range. Upon disconnection, the user device 302b and the wearable 304b, may both move to "abnormal" state (i.e., sounding an audible alarm). In embodiments, the disconnection may result in only one of the user device 302 or the wearable 304 moving to an abnormal state. However, as indicated by the use case of user device 302b and wearable 304b, both may sound an alarm upon disconnection. The detection of the disconnection and the generation of the alarm may occur as described herein.

The user device 302c and the wearable 304c may then reconnect, following, for example, the disconnection described at user device 302b and wearable 304b. The user device 302c and the wearable 304c may each return to a normal, non-alarm state. In embodiments, as depicted herein, the return to normal state may be facilitated by the reestablishment of the BLUETOOTH or other network reconnection between the user device 302c and the wearable 304c. In embodiments, the return to normal state can also occur via input from a user at the user device 302c or the wearable 304c. For example, in response to the alarm sounding, due to a disruption in the BLUETOOTH connection of user device 302b and wearable 304b, a user could notice that his child has wandered too far away. In response, the user could then disable the alarm via a swipe or tap on a screen of the user device 302b, causing a return to the normal state, as in user device 302c.

While still connected to the user device 302d, over for example, a BLUETOOTH network, the wearable 304d could determine, based on for example, environment data obtained from sensors on the wearable, that an unsafe temperature has been reached at the wearable (for example, based on the determination that a safety alert parameter has been met). The determination could be made as described in, for example, FIGS. 1 and 2. In embodiments, this determination could cause the generation of an audible alarm that could cause one or both of the wearable 304d and the user device 302d to move from a normal state to an abnormal, alarm state.

Figure 4:
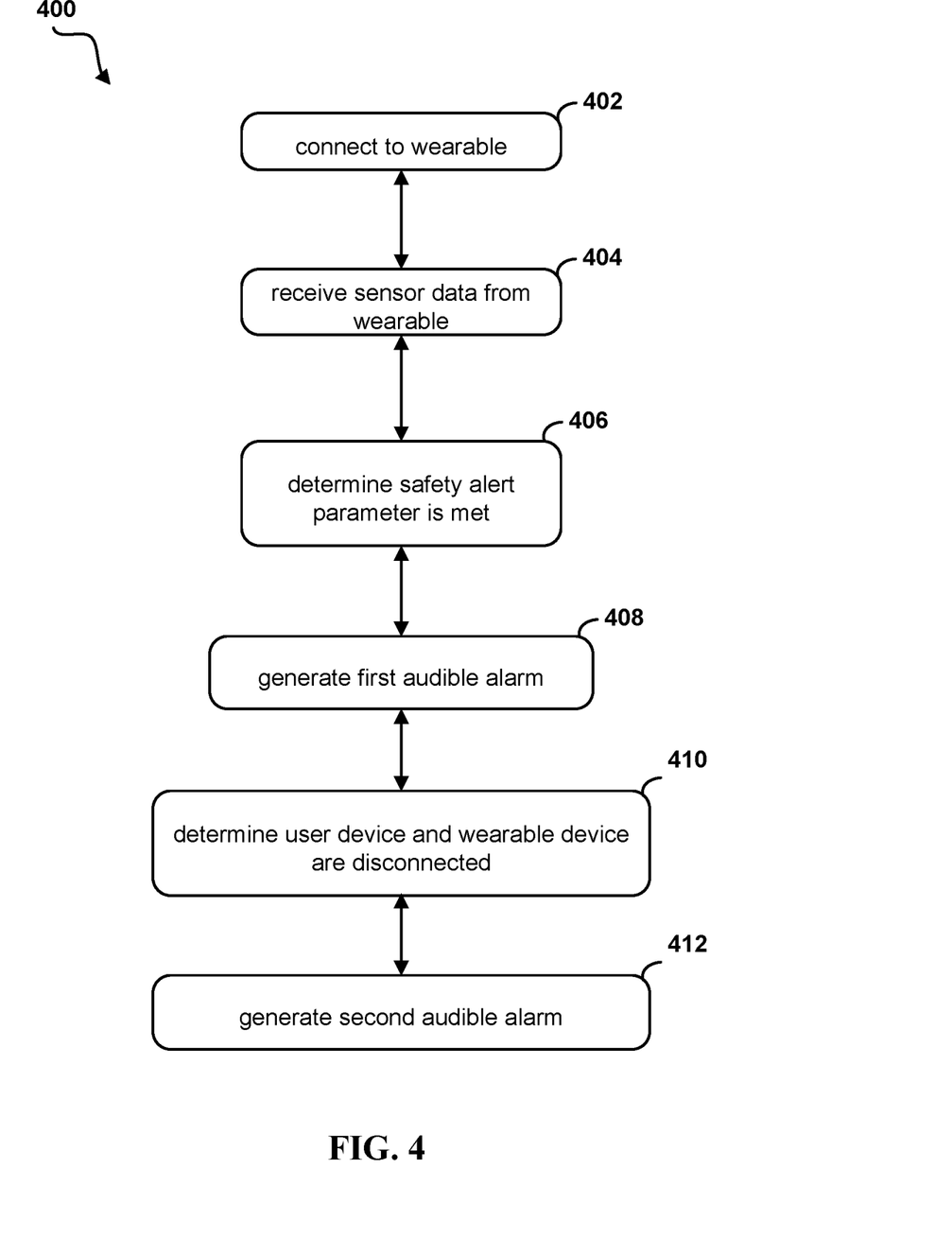
FIG. 4 depicts a flow diagram of a method for alerting a user of a user device, according to embodiments.

FIG. 4 depicts a flow diagram of a method 400 for alerting a user of a user device, according to embodiments. The method 400 may be performed by a computer system, for example computer system 102 of FIG. 1, and for purposes of description of the figure may be embodied as a user device, such as a smart phone. The method 400 may begin at 402 when the user device connects to the wearable over a short-range wireless connection. Once connected, the user device may receive sensor data from the wearable, per 404. As described herein, this sensor data may include data collected from sensors on or in communication with the wearable. The user device may then determine that a safety alert parameter has been met, per 406. In embodiments, the determining may include detecting a set of temperature data in the received sensor data, and comparing with a threshold temperature the set of temperature data. The threshold temperature may be a type of safety alert parameter. Based on the comparing, the system can determine that the temperature at the wearable exceeds the threshold temperature, and may thus be an unsafe temperature. In embodiments, the unsafe temperature may be determined based on a temperature unsafe for a child, for a pet, or for another relevant reason.

In embodiments, the device may generate a first audible alarm based on the determination, per 408. In embodiments, the user device may also display the alarm notification via a text-based alert, an image, a photograph, a combination of these elements, or in another way suitable for alerting the user. The system may also generate metadata which may indicate that the particular safety parameter has been met. The system may then transmit the metadata, to the wearable, to generate a notification that a safety alert parameter has been met. In embodiments, this can include an alarm as described for the user device. The notification could also indicate the particular type of safety alert parameter that has been met. For example, in response to sensor data from a temperature sensor on the wearable, the device can generate an alarm as well as a notification and transmit a notification that the wearable that the alarm is sounding based on an unsafe temperature. The device may also determine that the user device has been disconnected from the wearable, per 410. Based on this disconnection, the user device may then generate an audible alarm, per 412.

Figure 5:
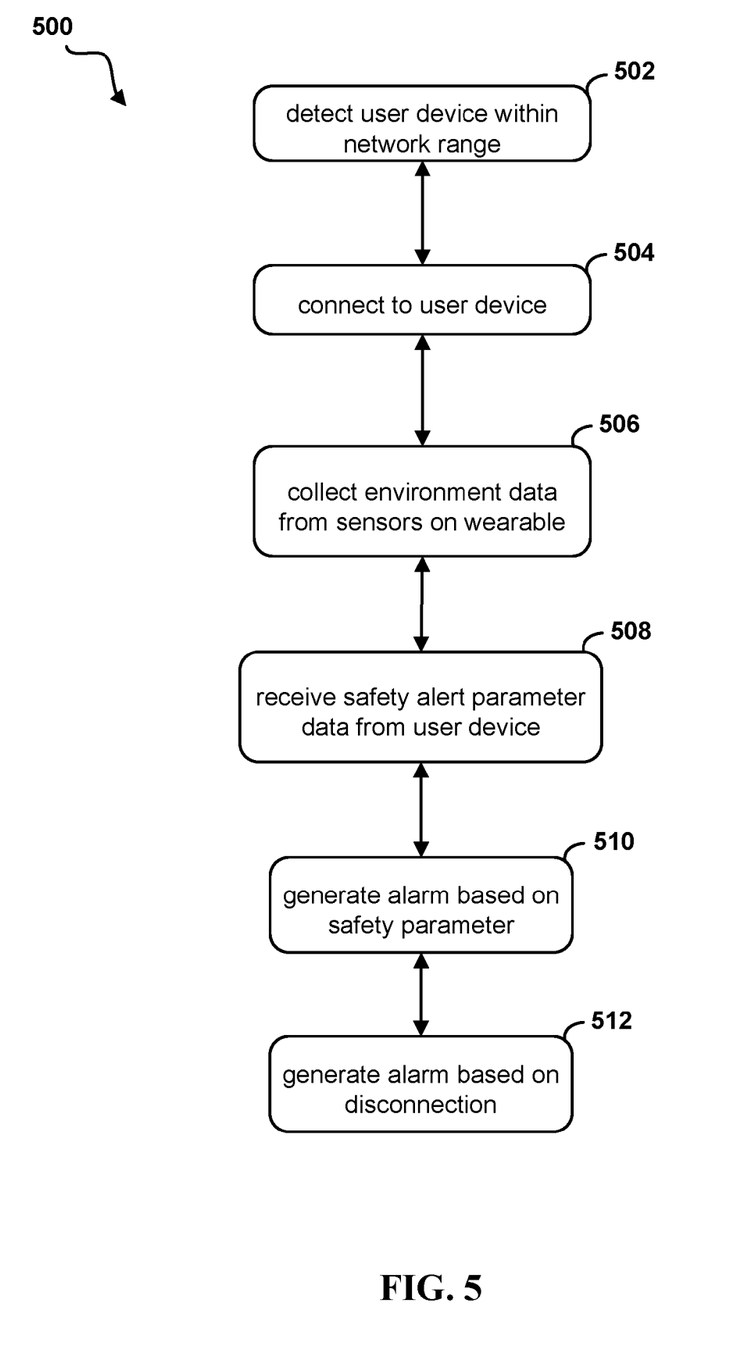
FIG. 5 depicts a flow diagram of a method for alerting a user of a wearable, according to embodiments.

FIG. 5 depicts a flow diagram of a method 500 for alerting a user of a wearable, according to embodiments. The method 500 may be carried out over a wearable, for example, wearable 206 of FIG. 2. The wearable may detect a user device within range of, for example, a short-range wireless connection, per 502. The wearable may then connect with the user device, per 504. Throughout its use, the wearable may collect environment data from sensors on or associated with it, per 506. The wearable may also receive safety alert parameter data from the user device, per 508. In embodiments, the user device could send the wearable data input by a user of the device (e.g., a smartphone user) regarding safety parameters for which the user was concerned. In embodiments, these parameters could vary based on the type and function of the wearable, the intended user of the wearable, or other parameters. Using the parameters and the environment data, the wearable may determine that a safety parameter has been met, and in response, the wearable may generate an alarm, per 510. In embodiments, a different alarm may be generated for each safety parameter. For example, if an alarm is triggered based on water exposure, a particular tone may sound, while an alarm based on temperature could trigger a different alarm. Notification of the safety alert parameter similar to those described at FIG. 4 may also originate at the wearable and be transmitted over the wireless connection to, for example, a user device in which the computer system (for example, the computer system 102 of FIG. 1) is embodied. A wearable may also detect when it has become disconnected from the user device over the wireless network. In embodiments, this disconnection may indicate that the wearable and the user device are too far apart to be connected by the short-range wireless (e.g., BLUETOOTH) connection. This disconnection may cause the wearable to generate an alarm, per 512.

Figure 6:
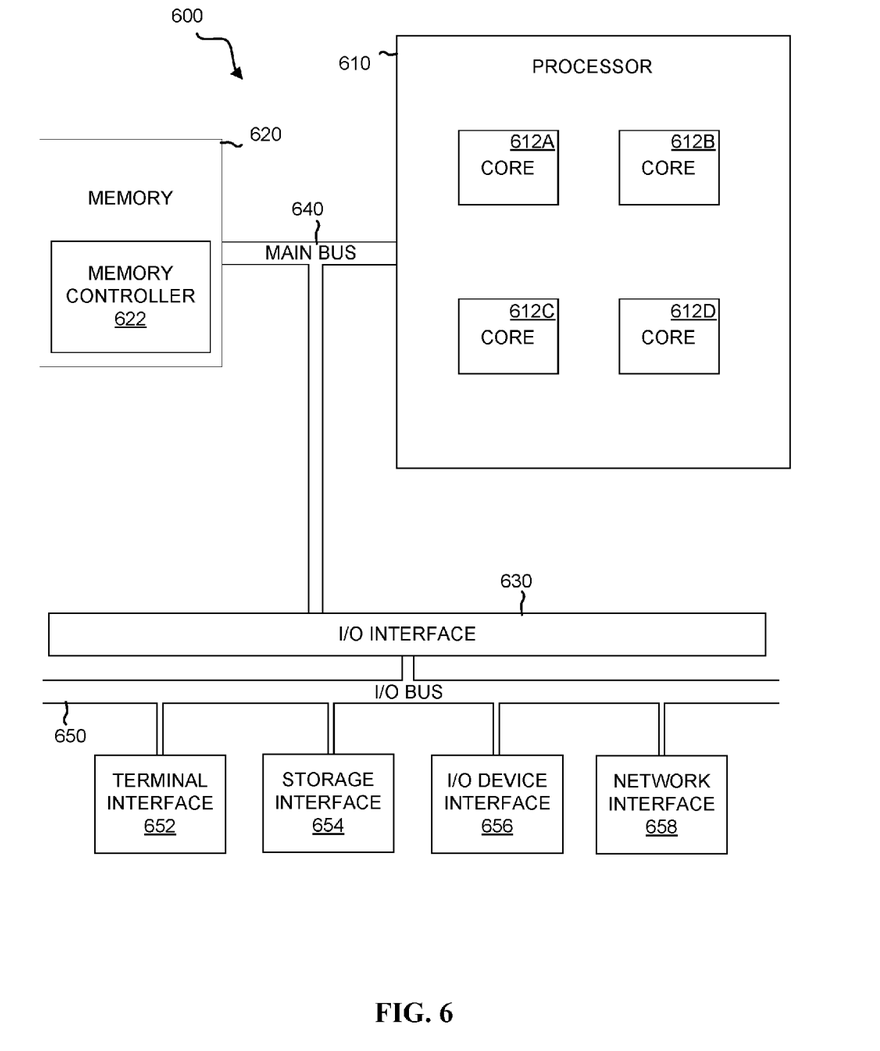
FIG. 6 is a block diagram illustrating a computer system, according to embodiments of the disclosure.

FIG. 6 depicts the representative major components of an example computer system 600 that may be used, in accordance with embodiments of the present disclosure. It is appreciated that individual components may vary in complexity, number, type, and\or configuration. The particular examples disclosed are for example purposes only and are not necessarily the only such variations. The computer system 600 may comprise a processor 610, memory 620, an input/output interface (herein I/O or I/O interface) 630, and a main bus 640. The main bus 640 may provide communication pathways for the other components of the computer system 600. In some embodiments, the main bus 640 may connect to other components such as a specialized digital signal processor (not depicted).

The processor 610 of the computer system 600 may be comprised of one or more cores 612A, 612B, 612C, 612D (collectively 612). The processor 610 may additionally include one or more memory buffers or caches (not depicted) that provide temporary storage of instructions and data for the cores 612. The cores 612 may perform instructions on input provided from the caches or from the memory 620 and output the result to caches or the memory. The cores 612 may be comprised of one or more circuits configured to perform one or methods consistent with embodiments of the present disclosure. In some embodiments, the computer system 600 may contain multiple processors 610. In some embodiments, the computer system 600 may be a single processor 610 with a singular core 612.

The memory 620 of the computer system 601 may include a memory controller 622. In some embodiments, the memory 620 may comprise a random-access semiconductor memory, storage device, or storage medium (either volatile or non-volatile) for storing data and programs. In some embodiments, the memory may be in the form of modules (e.g., dual in-line memory modules). The memory controller 622 may communicate with the processor 610, facilitating storage and retrieval of information in the memory 620. The memory controller 622 may communicate with the I/O interface 630, facilitating storage and retrieval of input or output in the memory 620.

The I/O interface 630 may comprise an I/O bus 650, a terminal interface 652, a storage interface 654, an I/O device interface 656, and a network interface 658. The I/O interface 630 may connect the main bus 640 to the I/O bus 650. The I/O interface 630 may direct instructions and data from the processor 610 and memory 620 to the various interfaces of the I/O bus 650. The I/O interface 630 may also direct instructions and data from the various interfaces of the I/O bus 650 to the processor 610 and memory 620. The various interfaces may include the terminal interface 652, the storage interface 654, the I/O device interface 656, and the network interface 658. In some embodiments, the various interfaces may include a subset of the aforementioned interfaces (e.g., an embedded computer system in an industrial application may not include the terminal interface 652 and the storage interface 654).

Logic modules throughout the computer system 600— including but not limited to the memory 620, the processor 610, and the I/O interface 630—may communicate failures and changes to one or more components to a hypervisor or operating system (not depicted). The hypervisor or the operating system may allocate the various resources available in the computer system 600 and track the location of data in memory 620 and of processes assigned to various cores 612. In embodiments that combine or rearrange elements, aspects and capabilities of the logic modules may be combined or redistributed. These variations would be apparent to one skilled in the art.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method comprising:
   connecting a user device to a wearable device using a short-range wireless connection;
   receiving, from the wearable device and through the short-range wireless connection, sensor data, the sensor data collected by at least one sensor on the wearable device;
   determining a safety alert parameter has been met based on the received sensor data;
   generating a first audible alarm in response to the determining the safety alert parameter has been met;
   determining the connection between the user device and the wearable device has been disconnected; and
   generating a second audible alarm in response to the determining the connection has been disconnected, wherein the determining the safety alert parameter has been met comprises:
   detecting, from the sensor data received from the wearable, a set of temperature data;
   comparing, with a threshold temperature, the data in the set of temperature data, wherein the threshold temperature data is the safety alert parameter; and
   determining the temperature at the wearable, as indicated by the temperature data exceeds a threshold temperature, the threshold temperature determined to be an unsafe temperature.

2. The method of claim 1, wherein the safety alert parameter includes a timing parameter.

3. The method of claim 1, wherein the method further comprises, in response to generating the first audible alarm, generating metadata indicating the safety alert parameter met is a temperature-based safety alert parameter; and transmitting the metadata to the wearable.

4. The method of claim 1, wherein the sensor data is obtained from a set of liquid sensors on the wearable.

5. The method of claim 1, wherein the short-range wireless connection is a BLUETOOTH connection.

6. The method of claim 1, wherein the wearable device is a smart watch.

7. A computer system comprising:
   a computer readable storage medium with program instructions stored thereon;
   a speaker; and
   one or more processors configured to execute the program instructions to perform a method comprising:
   connecting a user device to a wearable device using a short-range wireless connection;
   receiving, from the wearable device and through the short-range wireless connection, sensor data, the sensor data collected by at least one sensor on the wearable device;
   determining a safety alert parameter has been met based on the received sensor data;
   generating a first audible alarm in response to the determining the safety alert parameter has been met;
   determining the connection between the user device and the wearable device has been disconnected; and
   generating a second audible alarm in response to the determining the connection has been disconnected, wherein the determining the safety alert has been met comprises:
   detecting, from the sensor data received from the wearable, a set of temperature data;
   comparing, with a threshold temperature, the data in the set of temperature data, wherein the threshold temperature data is the safety alert parameter; and
   determining the temperature at the wearable, as indicated by the temperature data exceeds a threshold temperature, the threshold temperature determined to be an unsafe temperature.

8. The system of claim 7, wherein the method further comprises, in response to the generating the first audible alarm, generating metadata indicating the safety alert parameter met is a temperature-based safety alert parameter.

9. The system of claim 7, wherein the sensor data is obtained from a set of liquid sensors on the wearable.

10. The system of claim 7, wherein the wearable is a heart rate monitor.

* * * * *